United States Patent
Altagracia Martínez et al.

(10) Patent No.: US 8,680,156 B2
(45) Date of Patent: Mar. 25, 2014

(54) SOLUBLE PHARMACEUTICAL FORMULATIONS OF N,N'-DIAMINODIPHENYL SULFONE FOR OPTIMAL USE IN THE TREATMENT OF VARIOUS DISEASES

(75) Inventors: Marina Altagracia Martínez, México, D.F. (MX); Luis Camilo Ríos Castañeda, México, D.F. (MX); Jaime Kravzov Jinich, México, D.F. (MX); Maria de los Ángeles Araceli Díaz Ruíz, México, D.F. (MX)

(73) Assignee: Universidad Autonoma Metropolitana, Mexico D.F. (MX)

( * ) Notice: Subject to any disclaimer, the term of this patent is extended or adjusted under 35 U.S.C. 154(b) by 2 days.

(21) Appl. No.: 13/266,892

(22) PCT Filed: Oct. 5, 2009

(86) PCT No.: PCT/MX2009/000105
§ 371 (c)(1),
(2), (4) Date: Mar. 8, 2012

(87) PCT Pub. No.: WO2010/126349
PCT Pub. Date: Nov. 4, 2010

(65) Prior Publication Data
US 2012/0157541 A1    Jun. 21, 2012

(30) Foreign Application Priority Data

Apr. 29, 2009 (MX) .................. MX/a/2009/004635

(51) Int. Cl.
*A61K 31/135* (2006.01)
(52) U.S. Cl.
USPC ....................................................... 514/646

(58) Field of Classification Search
USPC ......................................................... 514/646
See application file for complete search history.

(56) References Cited

U.S. PATENT DOCUMENTS

2006/0204526 A1    9/2006 Lathrop et al.

FOREIGN PATENT DOCUMENTS

WO    WO 2009/108147 A1    9/2009

OTHER PUBLICATIONS

Mirochnick et al., "Bioequivalence of a propylene glycol-based liquid dapsone preparation and dapsone tablets", Am. J. Health-Syst Pharm, vol. 57 (2000) pp. 1775-1777.
Mirochnick et al., "Pharmacokinetics of dapsone in children", The Journal of Pediatrics, vol. 122, No. 5, part 1 (1993) pp. 806-809.
Nahata et al., "Stability of Dapsone in Two Oral Liquid Dosage Forms", The Annals of Pharmacotherapy, vol. 34 (2000) pp. 848-850.

*Primary Examiner* — Raymond Henley, III
(74) *Attorney, Agent, or Firm* — Birch, Stewart, Kolasch & Birch, LLP

(57) ABSTRACT

The present invention aims to demonstrate that a soluble pharmaceutical formulation can be prepared of N,N'-Diamino-diphenyl sulfone which is useful in the development of an ideal drug for use against cerebral infarction, epilepsy, traumatic spinal cord injury, cranio-encephalic trauma, leprosy, *Pneumocystis carinii* infections and any condition which requires rapid and complete absorption of the compound. As a representative example of this application, the dissolution of N,N'-Diamino-diphenyl sulfone was evaluated as a neuroprotector in a model of acute cerebral infarction in rats. In this study, N,N'-Diamino-diphenyl sulfone showed significant prevention of brain damage, without presenting adverse effects in animals. It is also shown that the soluble pharmaceutical formulations prepared in this manner produce peak blood levels 30 minutes from oral administration and immediately via the intravenous route.

12 Claims, 3 Drawing Sheets

SOLUBLE PHARMACEUTICAL FORMULATIONS OF N,N'-DIAMINODIPHENYL SULFONE FOR OPTIMAL USE IN THE TREATMENT OF VARIOUS DISEASES

THE FIELD OF THE INVENTION

The present invention is related to the pharmaceutical production industry, and more specifically to the industry of manufacturing medications to various diseases.

BACKGROUND

Chemotherapeutic treatment of leprosy and *Pneumocystis carinii* infections is performed by the administration of pills of N,N'-diamino-diphenyl sulfone. The pharmaceutical formulation of the sulfone in solution for use as a drug poses technical problems due to the low solubility of N,N'-diamino-diphenyl sulfone in an aqueous medium, therefore, in the present invention, new formulations are presented that allow solubilization of up to 200 mg of sulfone/3 mL, using co-solvents that are compatible with pharmaceutical safe use in humans.

N,N'-diamino-diphenyl sulfone solutions have been reported using the surfactant compound Tween-80, in a ratio of 90% [Helton D R, Osborne D W, Pierson S K, Buonarati M H, Bethem R A., Pharmacokinetic profiles in rats after intravenous, oral, or dermal administration of dapsone, Drug Metabolism and Disposition 28: 925-929 (2000)], Drug Metabolism and Disposition 28: 925-929 (2000)], with the serious disadvantage that Tween-80 is a toxic compound at the necessary concentrations to dissolve sulfone, which precludes its use in humans.

The present invention has the purpose of achieving water-soluble mixtures of N,N'-diamino-diphenyl sulfone for faster absorption of the active molecule with the possibility of applying it in unconscious people and that allows its safe use in human beings as a medication for therapeutic administration in the form of solutions by any systemic route, including all enteral and parenteral routes.

N,N'-diamino-diphenyl sulfone is a drug currently used in the chemotherapy of leprosy and in the prophylaxis against *Pneumocystis carinii* pneumonia. Recently, N,N'-diamino-diphenyl sulfone (dapsone) has shown other uses as a neuro-protective and anti-epileptic, which frequently require administration to unconscious patients, making it impossible for the administration of solid pharmaceutical formulations. These new applications for dapsone have been patented (patent No. MX 246.892, patent No. MX 264.912) and the soluble forms are more suitable for such applications, because faster drug absorption is required in treatments, compared with the speed of solid formulations.

SUMMARY

The present invention describes a product for therapeutic use based on the dissolution of N,N'-diamino-diphenyl sulfone in a mixture of solvents compatible with its medicinal use in humans. The N,N'-diamino-diphenyl sulfone is used with new applications that frequently require administration to unconscious patients, therefore, the solid formulations of the drug currently in use are unsuitable.

Searching for options to dissolve N,N'-diamino-diphenyl sulfone, it was found that mixtures of ethanol/propylene-glycol/glycofurol/benzyl alcohol/water with various additives such as thickeners, stabilizers and/or flavorings, allow for obtaining stable products perfectly suited for administration by any enteral or parenteral routes. The solutions were obtained by synthesis of N,N'-diamino-diphenyl sulfone, a compound with the following formula:

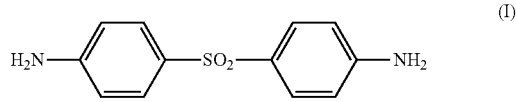 [SMILES: Nc1ccc(S(=O)(=O)c2ccc(N)cc2)cc1]

(I)

In all cases, USP-grade solvents and reagents were used, free of pyrogens.

The dissolution tests were carried out in glass or stainless steel containers in volumes of 10 mL to 5 L, placing mixtures of co-solvents with 200 mg of N,N'-diamino-diphenyl sulfone/3 mL. The N,N'-diamino-diphenyl sulfone dissolution was determined by visual inspection of the containers, after vigorous shaking.

A simplex algorithm was used to determine the optimum ratio of mixtures of ethanol/propylene glycol/glycofurol/benzyl alcohol/water needed to dissolve the N,N'-diamino-diphenyl sulfone.

For stability studies of the N,N'-diamino-diphenyl sulfone solution, glass vials were used with 10 ml capacity, sealed with a gas burner.

Sterilization of vials with the soluble formula was performed in an autoclave at 110° C.

DETAILED DESCRIPTION

Synthesis of N,N'-diamino-diphenyl sulfone

Figure 1:
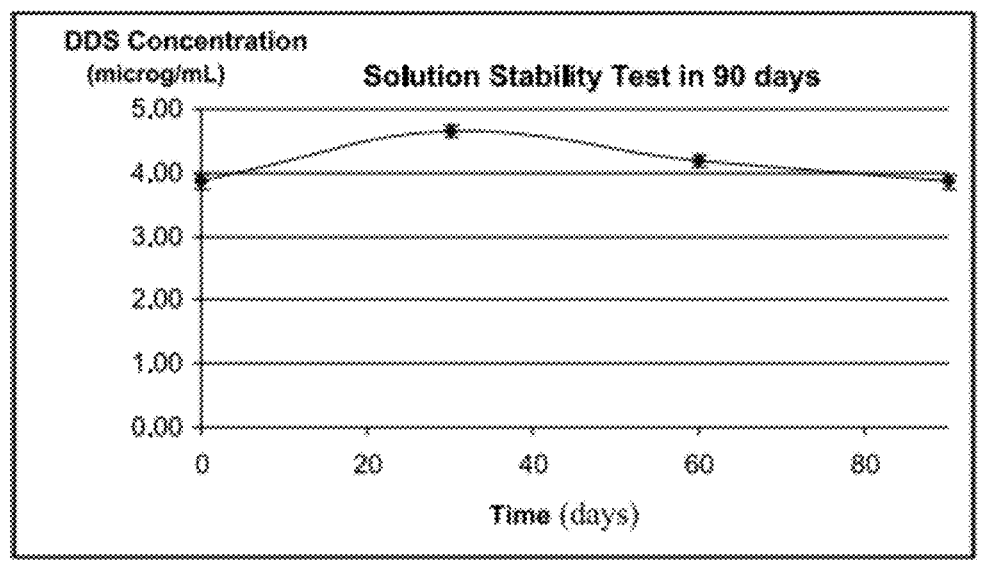
FIG. 1 illustrates the graph representing time in days on the x-axis, and the DDS concentration on the y-axis.

N,N'-Diamino-diphenyl sulfone can be synthesized in various ways, but the following synthesis route is offered as an example.

This synthesis was performed in two steps:

1. 60 g of acetanilide were poured into an Erlenmeyer flask and heated slowly with flame until the melting of the solid was complete. The resulting viscous liquid was cooled in a glass of ice, ensuring that the solidified material stayed at the bottom of the flask. 165 ml of chloro-sulfonic acid were added in a single portion, without removal from the ice bath. Subsequently, the flask was removed from the ice, mixing carefully, and the reaction was allowed to be take place for 10 minutes, at the end of which the reaction mixture was again heated until the total solubilization of the remaining acetanilide, allowing it to react again for 10 more minutes. The product was allowed to cool and was carefully poured into a container with ice and water, filtering the precipitate and washing it with cold water. The precipitate was collected, dissolved in chloroform and extracted three times with water, collecting the chloroform phase, which was placed in an ice bath, precipitating the purified thionyl chloride (Reported melting point of the intermediary: 149° C.).

2. 123.6 ml of anhydrous nitrobenzene were poured into a glass reactor, 89.2 g of aluminum chloride were added and heated slowly; then, 41.3 g of thionyl chloride was added to the hot mixture, heating the reaction mixture at a temperature of 140-145° C., and 13 g of acetanilide were slowly added, maintaining the reaction temperature for two hours. At the end of this period, the product of the reaction was poured into 104 ml of water acidified with hydrochloric acid then dark crystals were precipitated, and were recrystallized with dilute acetic acid. These crystals were refluxed with 5N hydrochloric acid for 30 minutes, then neutralizing the reaction mixture, with which white crystals were precipitated (raw DDS), which was recrystallized again with ethanol.

Chemical Characterization of the Synthesized Compound.

To determine the authenticity of the synthesized compounds, their melting point thereof were obtained, which was from 151 to 153° C. for the reaction intermediary of thionyl chloride, and from 172 to 175° C. for DDS.

The melting points reported for these compounds are 149° C., 175-176° C. for the intermediary and the DDS, respectively.

PREFERRED MODE OF CARRYING OUT THE INVENTION

The use of ethanol/propylene glycol/glycofurol/benzyl alcohol/water in varying proportions to the solution of N,N'-Diamino-diphenyl sulfone is useful for preparing a medication against various diseases, such as cerebral infarction, epilepsy, traumatic spinal cord injury, cranio-encephalic injury, cerebral hemorrhage, subarachnoid hemorrhage due to aneurysm, leprosy, *Pneumocystis carinii* infections and any condition that requires a rapid and complete absorption of the compound, administered by any systemic route.

Drug administration can be carried out in dosages of 0.2 mg/Kg to 12 mg/Kg and can be repeated as often as necessary for periods from 1 to 7 days.

EXAMPLE 1

Dissolution of N,N'-Diamino-Diphenyl Sulfone for Administration as a Solution for Administration by any Enteral or Parenteral Route From 50 mg to 500 g of N,N'-diamino-diphenyl sulfone are weighed and placed in a test tube. 5 volumes of a mixture containing 2.9 volumes of propylene glycol, 1.25 volumes of Ethanol and 0.85 volumes of water are added. They are shaken until achieving the complete dissolution of the N,N'-diamino-diphenyl sulfone.

The solution obtained is transferred to a glass vial which is then sealed and sterilized by autoclave.

To determine whether the dissolution of N,N'-diamino-diphenyl sulfone was complete and whether the sterilization procedure caused an appreciable degradation of N,N'-diamino-diphenyl sulfone, the solutions of N,N'-diamino-diphenyl sulfone were analyzed with high-resolution liquid chromatography with ultraviolet light detection.

Evaluation of the Neuroprotective Effect of Soluble Formulations of N,N'-Diamino-Diphenyl-Sulfone.

To evaluate the neuroprotective capacity of the soluble formulations of dapsone, its effect was tested in a model of brain ischemia in rats. In this model, there was permanent cerebral ischemia in rats due to permanent occlusion of the middle cerebral artery, as described below:

Selective permanent brain ischemia was produced in animals by the introduction of an intraluminal suture through the carotid artery. All animals received continuous anesthesia during the surgical procedure, with 1.5% Halothane through a face mask. The animals were placed in the supine position, the anterior cervical region was fixed and shaved in order to make an incision in the midline of the manubrium sterni to the sternohyoid muscle region and was continued to its lateral edge, identifying in this site the medial border of the sternocleidomastoid and superficial cervical fascia in the deep layer, which was influenced to expose the common carotid below and within the di-gastric belly flow.

A sharp dissection of the common carotid was made to the hypoglossal loop. The carotid bifurcation, the external carotid artery and its occipital and thyroid branches were identified, and the latter two were tied with 8-0 monofilament, as well as with electro-coagulation for its posterior cut. The internal carotid artery was dissected over a length of about 5 mm, and at that time, the pterygopalatine artery was identified. A microchip was placed in it, or alternatively, it was tied with 6-0 monofilament. After removing the flow through these arterial tributaries, 3-0 nylon monofilament was introduced in the direction towards the internal carotid artery, through the stump of the external carotid artery, at a length of 17 mm from the bifurcation. The wound was closed and the animal was allowed to recover with food and water on demand. In all cases, ischemia was confirmed by macroscopic observation and by the position of the thread.

Evaluation of the Neuroprotective Effect of Soluble Formulations of N,N'-Diamino-Diphenyl-Sulfone in Rats.

Serial histological sections were made from the brains of the rats, performing the stain of hematoxylin and eosin, to determine the area of injury. The representative result of this neuroprotective effect, for animals treated with the new pharmaceutical forms, and the effect of the vehicles, is shown in FIG. 2.

Figure 2:
FIG. 2 shows a histological section of a rat brain in which cerebral infarction was produced, and only the drug vehicles were applied.

FIG. 2 shows that the area of injury is significantly lower in animals treated with the new soluble forms of N,N'-Diamino-diphenyl sulfone, compared to control animals treated with the vehicle.

Pharmacokinetic Profile of Soluble Pharmaceutical Formulations of N,N'-Diamino-Diphenyl Sulfone in Healthy Volunteers.

Figure 3:
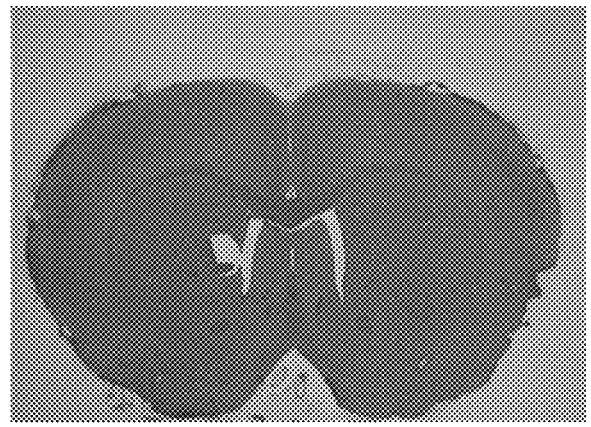
FIG. 3 shows a histological section of a rat brain in which cerebral infarction was produced and the solution was applied intravenously.
Figure 4:
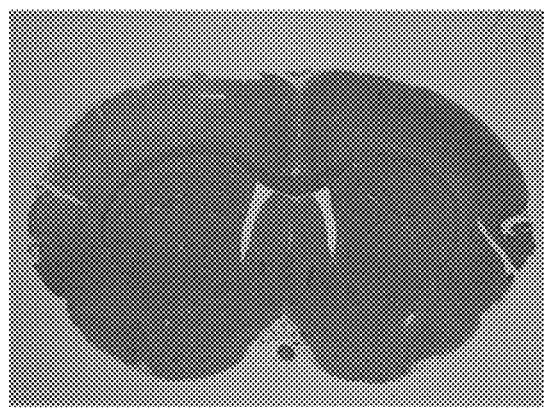
FIG. 4 shows a histological section of a rat brain in which cerebral infarction was produced and the oral solution was applied.
Figure 5:
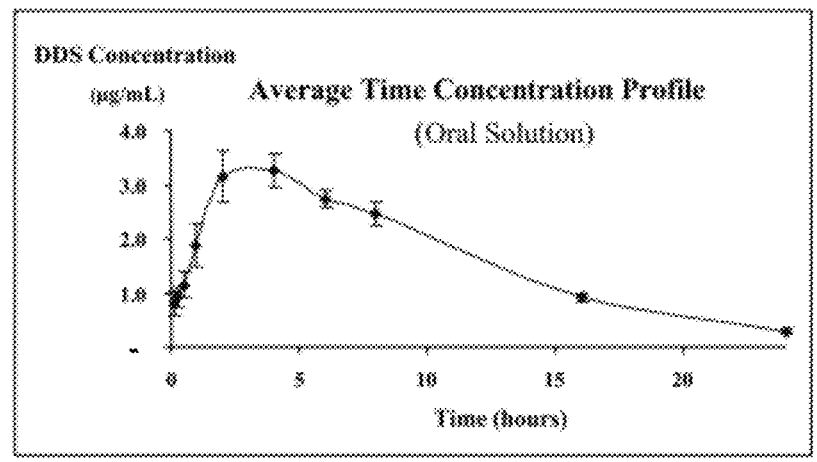
FIG. 5 shows the plasma concentration profile when the oral formulation is applied.
Figure 6:
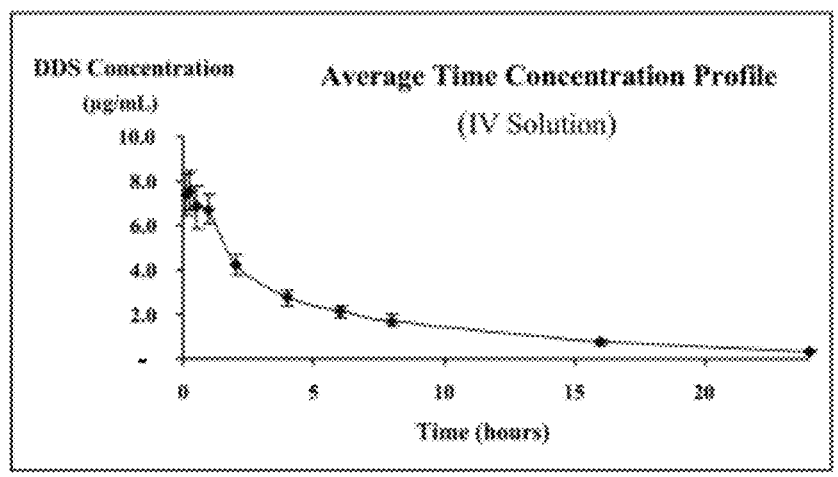
FIG. 6 shows the plasma concentration profile when the formulation is applied intravenously.

Soluble forms of N,N'-Diamino-diphenyl sulfone (DDS) were administered in solution both orally (FIG. 3), as well as intravenously (FIG. 4) in 18 healthy human volunteers, and the plasma concentrations of N,N'-Diamino-diphenyl sulfone were determined at different times. FIGS. 3 and 4 show the results of that analysis.

After calculating the area under the curve of the pharmacokinetic profiles for each rat, average bioavailability of more than 92% was obtained for the oral form, taking the area under the curve of the intravenous route as 100% bioavailability. This result indicates that the soluble oral form is absorbed optimally in the digestive tract. The maximum concentration for the oral form is obtained on average in a half-hour, while reports in the literature indicate a time to reach maximum plasma concentration of 2 to 3 hours for the solid forms (Breen G A, Brocavich J M, Etzel J V, Shah V, Schaefer P, Forlenza S., Evaluation of effects of altered gastric pH on absorption of dapsone in healthy volunteers, Antimicrobial Agents and Chemotherapy 1994 September; 38(9):2227-2229)

What is claimed is:

1. A solution of N,N'-Diamino-diphenyl sulfone, in a mixture of a) ethanol/b) propylene glycol/c) glycofurol/d) benzyl alcohol/e) water for therapeutic purposes, wherein said mixture contains:
   a) ethanol in the range of 0 to 25%;
   b) propylene glycol in the range of 0 to 60%;
   c) glycofurol in the range of 0 to 25%;
   d) benzyl alcohol in the range of 0 to 20%; and
   e) water in the range of 5 to 90%.

2. The solution of claim 1, wherein said solution contains amounts for administering dosages to an individual of 0.2 mg/Kg of the individual to 12 mg/Kg of the individual.

3. The solution of claim 2, wherein said mixture contains:
   a) Ethanol 25%;
   b) Propylene glycol 58%;
   c) Glycofurol 5%;
   d) Benzyl Alcohol 1%; and
   e) Water 11%.

4. A method for treatment of a disease selected from the group consisting of cerebral infarction, epilepsy, traumatic spinal cord injury, cranio-encephalic trauma, cerebral hemorrhage, leprosy, and *Pneumocystis carinii* infections, comprising the step of:
   administering the solution of claim 1 to a patient in need thereof.

5. The method of claim 4, wherein the solution is administered at doses between 5 and 300 mg per day.

6. The method of claim 4, where the administration is repeated every 24 hours.

7. A method for treatment of a disease selected from the group consisting of cerebral infarction, epilepsy, traumatic spinal cord injury, cranio-encephalic trauma, cerebral hemorrhage, leprosy, and *Pneumocystis carinii* infections, comprising the step of:
   administering the solution of claim 2 to a patient in need thereof.

8. A method for treatment of a disease selected from the group consisting of cerebral infarction, epilepsy, traumatic spinal cord injury, cranio-encephalic trauma, cerebral hemorrhage, leprosy, and *Pneumocystis carinii* infections, comprising the step of:
   administering the solution of claim 3 to a patient in need thereof.

9. The method of claim 7, wherein the solution is administered at doses between 5 and 300 mg per day.

10. The method of claim 8, wherein the solution is administered at doses between 5 and 300 mg per day.

11. The method of claim 7, where the administration is repeated every 24 hours.

12. The method of claim 8, where the administration is repeated every 24 hours.

* * * * *